United States Patent [19]
Kobayashi et al.

[11] Patent Number: 6,114,485
[45] Date of Patent: Sep. 5, 2000

[54] THIOL AND SULFUR-CONTAINING O-(METH)ACRYLATE COMPOUNDS AND USE THEREOF

[75] Inventors: Seiichi Kobayashi, Kanagawa; Nobuya Kawauchi, Tokyo; Toshiyuki Suzuki, Kanagawa; Masao Imai, Kanagawa; Kenichi Fujii, Kanagawa, all of Japan

[73] Assignee: Mitsui Chemicals, Inc., Japan

[21] Appl. No.: 09/157,985

[22] Filed: Sep. 22, 1998

Related U.S. Application Data

[62] Division of application No. 08/861,024, May 21, 1997, Pat. No. 5,916,987.

[30] Foreign Application Priority Data

May 29, 1996 [JP] Japan ..................................... 8-135515
May 30, 1996 [JP] Japan ..................................... 8-136504

[51] Int. Cl.$^7$ .......................... C08F 22/24; C07C 327/00; G02C 7/02
[52] U.S. Cl. ........................... 526/289; 351/159; 558/251
[58] Field of Search ........................... 526/289; 558/251; 359/321, 577; 351/159

[56] References Cited

U.S. PATENT DOCUMENTS 2,582,605  1/1952  Richter ..................................... 560/221
2,925,406  2/1960  McCurdy et al. ...................... 526/289

(List continued on next page.)

FOREIGN PATENT DOCUMENTS 336361  10/1989  European Pat. Off. .
382777   8/1990  European Pat. Off. ................ 526/289

(List continued on next page.)

*Primary Examiner*—Veronica P. Hoke
*Attorney, Agent, or Firm*—Burns, Doane, Swecker, & Mathis, L.L.P.

[57] ABSTRACT

A sulfur-containing O-(meth)acrylate compound of the following formula (1) is useful as a starting material for a resin composition used in optical applications such as a lens;

$$A \text{---} \left[ B \text{---} \left( S(CH_2)_l \text{---} O \text{---} \overset{O}{\underset{\|}{C}} \text{---} \overset{R}{\underset{|}{C}} = CH_2 \right)_n \right]_m \quad (1)$$

wherein R represents hydrogen atom or methyl group; l represents an integer from 1 to 3; B is $$-\text{CH} \diagdown, \quad -\overset{O}{\underset{\|}{C}}- \quad \text{or} \quad -\overset{}{\underset{H}{N}}-\overset{O}{\underset{\|}{C}}-;$$

when B is $$-\text{CH} \diagdown,$$

n is 2; m is 1 or 2; A is selected from the following groups:

[aromatic ring structures with substituents $(CH_2)_p$, $CH_3S(CH_2)_q$, naphthalene, and thiophene]

wherein m represents 1 or 2; each ring may be substituted by one or more alkyl, alkylthio or alkoxy groups having 1 or 2 carbon atoms; p and q are 0 or 1, while m is 1 when p is 1;

when B is $$-\overset{O}{\underset{\|}{C}}-,$$

n is 1; m is 2 or 3; A is selected from the following groups:

$-(CH_2)_r\text{---}S\text{---}(CH_2)_r\text{---}$, $-(CH_2)_r\text{---}S\text{---}S\text{---}(CH_2)_r\text{---}$,
$-(CH_2)_r\text{---}S\text{---}(CH_2)_s\text{---}S\text{---}(CH_2)_r\text{---}$ and $$\begin{array}{c} S\text{---}(CH_2)_r\text{---} \\ | \\ -(CH_2)_r\text{---}S\text{---}CH\text{---}S\text{---}(CH_2)_r\text{---} \end{array}$$

wherein r and s are an integer from 1 to 3;
when B is $$-\overset{}{\underset{H}{N}}-\overset{O}{\underset{\|}{C}}-,$$

n is 1; m is 2; A is selected from the following groups:

$-(CH_2)_r\text{---}S\text{---}(CH_2)_r\text{---}$, $-(CH_2)_r\text{---}S\text{---}S\text{---}(CH_2)_r\text{---}$ and
$-(CH_2)_r\text{---}S\text{---}(CH_2)_s\text{---}S\text{---}(CH_2)_r\text{---}$ wherein r and s are an integer from 1 to 3.

12 Claims, 5 Drawing Sheets

U.S. PATENT DOCUMENTS

| | | | |
|---|---|---|---|
| 3,265,673 | 8/1966 | Richards et al. | 526/289 |
| 3,412,076 | 11/1968 | Farber et al. | 526/289 |
| 4,340,707 | 7/1982 | Quis et al. | 526/289 |
| 4,775,733 | 10/1988 | Kanemura et al. | |
| 4,810,812 | 3/1989 | Matsuda et al. | |
| 4,931,521 | 6/1990 | Matsuda et al. | 526/289 |
| 4,939,218 | 7/1990 | Kawaki et al. | |
| 4,992,293 | 2/1991 | Klemann et al. | 558/251 |
| 5,064,495 | 11/1991 | Omura et al. | 526/289 |
| 5,183,917 | 2/1993 | Maruyama et al. | 558/251 |
| 5,247,041 | 9/1993 | Iguchi et al. | 526/289 |
| 5,270,439 | 12/1993 | Maruyama et al. | 528/373 |
| 5,384,379 | 1/1995 | Bader et al. | 526/289 |
| 5,399,735 | 3/1995 | Iguchi et al. | 558/251 |
| 5,424,339 | 6/1995 | Zanka et al. | 526/289 |
| 5,424,472 | 6/1995 | Bader et al. | 558/251 |
| 5,442,022 | 8/1995 | Keita | 526/289 |
| 5,488,128 | 1/1996 | Bader et al. | 558/251 |
| 5,674,960 | 10/1997 | Namdaran et al. | 526/289 |
| 5,683,628 | 11/1997 | Mizuno et al. | 252/586 |
| 5,702,825 | 12/1997 | Keita et al. | 526/289 |
| 5,741,831 | 4/1998 | Keita et al. | 526/289 |
| 5,917,006 | 6/1999 | Smith et al. | 525/191 |
| 5,969,867 | 10/1999 | Fukushima et al. | 359/581 |

FOREIGN PATENT DOCUMENTS

| | | | |
|---|---|---|---|
| 524477 | 1/1993 | European Pat. Off. | |
| 3321502 | 12/1984 | Germany | 526/289 |
| 63-046213 | 2/1988 | Japan | |
| 63-188660 | 8/1988 | Japan | |
| 01128966 | 5/1989 | Japan | |
| 03059060 | 9/1991 | Japan | |
| 03217412 | 9/1991 | Japan | |
| 3-205414 | 9/1991 | Japan | 526/289 |
| 4-11613 | 1/1992 | Japan | 526/289 |
| 04161410 | 6/1992 | Japan | |

THIOL AND SULFUR-CONTAINING O-(METH)ACRYLATE COMPOUNDS AND USE THEREOF

This application is a divisional, of application Ser. No. 08/861,024, filed May 21, 1997 now U.S. Pat. No. 5,916,987.

BACKGROUND OF THE INVENTION

1. Field of the Invention

This invention relates to a novel sulfur-containing O-(meth)acrylate compound; a process for preparation of the sulfur-containing O-(meth)acrylate compound, comprising dithioacetalization, thio-esterification or thiourethanization of a novel thiol compound followed by dehydrohalogenation; an optical resin composition comprising the sulfur-containing O-(meth)acrylate compound; and an optical resin prepared by polymerization of the composition.

2. Description of the Related Arts

A plastic lens is lighter and less brittle than an inorganic lens, and dyeable, which has been therefore rapidly gaining prevalence in the areas of optical devices such as lenses for eyeglasses and cameras. Currently, the resins which may be widely used for these applications, include those prepared by radical polymerization of diethylene glycol bis (allylcarbonate) (referred to as 'D.A.C.'). These resins have various features such as excellent impact resistance, lightness, excellent tintability, and good processability including machinability and abradability. These resins, however, have a low refractive index ($n_d$) of about 1.50 so that it is necessary to increase the center thickness and the edge thickness, and when such requirements are met, the lens is unavoidably thickened on the whole. Therefore, a lens having a higher refractive index has been desired.

Resins with a higher refractive index than D.A.C. resin are known; for example, polythiourethane resins (e.g., JP-A 63-46213); sulfur-containing O-(meth)acrylate resins (e.g., JP-A 1-128966, 3-217412 and 4-161410); and thio(meth)-acrylate resins (e.g., JP-A 63-188660 and JP-B 3-59060), in which sulfur atoms are introduced. A polythiourethane resin is well-balanced in its properties, that is, has a high refractive index and good impact resistance and the like. When rapidly polymerizing it, the resin, however, tends to be inhomogeneously polymerized, and thus the polymerization inevitably takes longer time to obtain an optically homogeneous lens. Furthermore, during processing it by cutting and abrasion, sulfur odor may generate.

A sulfur-containing O-(meth)acrylate resin or a thio (meth)acrylate resin can be prepared by rapid polymerization by means of UV rays or the like. In general, a resin produced may, however, have inadequate strength or impact resistance, that is, it may be brittle and breakable. Recently, a resin for a lens has been required to have processing strength suitable for a two-point processing widely used in the area of a lens for eyeglasses, and a center of a lens for eyeglasses has been being thinner. Thus, there has been a demand for a resin having higher strength and impact resistance. Furthermore, since a thio(meth)acrylate compound is less stable, it may gel or tend to be uncontrollably rapidly polymerized and require complex operations. Therefore, there has been a need for further improvement to solve these problems.

SUMMARY OF THE INVENTION

An objective of this invention is to provide an optical resin composition which has a good handling properties and can be rapidly polymerized, and which gives an optical resin having excellent optical properties, particularly a high refractive index and excellent impact resistance, as well as generating less unpleasant odor during processing. In seeking the above object and have found that some kind of sulfur-containing O-(meth)acrylate compounds are effective, it has been completed this invention. That is to say, this invention relates to a sulfur-containing O-(meth)acrylate compound of the following formula (1):

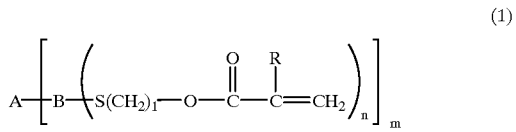

wherein R represents a hydrogen atom or methyl group; l represents an integer from 1 to 3; B is

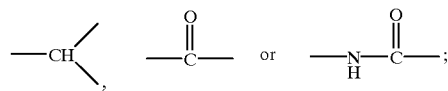

when B is

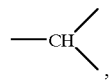

then n is 2; m is 1 or 2; A is selected from the following groups:

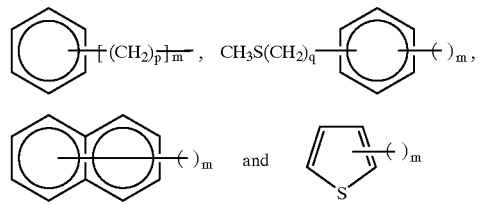

wherein m represents 1 or 2; each ring may be substituted by one or more alkyl, alkylthio or alkoxy groups having 1 or 2 carbon atoms; p and q are 0 or 1, while m is 1 when p is 1;

when B is

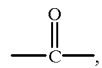

then n is 1; m is 2 or 3; A is selected from the following groups:

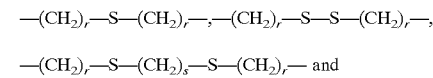

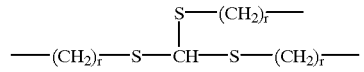

wherein r and s are an integer from 1 to 3;

when B is

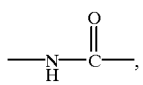

n is 1; m is 2; A is selected from the following groups;

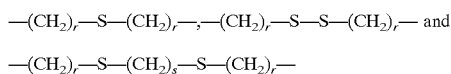

wherein r and s are an integer from 1 to 3

This invention also relates to a process for preparation of the sulfur-containing O-(meth)acrylate compound of the above formula (1), comprising dithioacetalizing a thiol compound represented by the following formula (2):

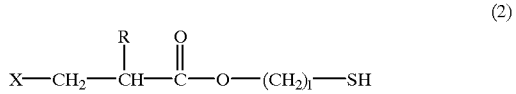 (2)

wherein X represents Cl or Br; R represents hydrogen atom or methyl group; and l represents an integer from 1 to 3, with a compound having at least one aldehyde group in its molecule; thioesterificating the thiol compound with a compound having at least two carboxyl groups in its molecule or thiourethanizing the thiol compound with a compound having at least two isocyanate groups in its molecule; and then dehydrohalogenating the product.

The compound of the above formula (2) is also novel, which, as an intermediate of the sulfur-containing O-(meth)acrylate of the above formula (1), is covered by this invention.

Further, this invention also relates to an optical resin composition comprising the sulfur-containing O-(meth)acrylate compound of the above formula (1), and a sulfur-containing resin and lens formed by polymerizing the composition.

The sulfur-containing O-(meth)acrylate compound of this invention is novel, has improved stability as a monomer and has excellent workability. The optical resin composition of this invention can be rapidly polymerized, giving an optical resin which has excellent optical properties, in particular a high refractive index and excellent impact resistance, as well as generates less unpleasant odor during processing.

DETAILED DESCRIPTION OF THE PREFERRED EMBODIMENTS

Figure 1:
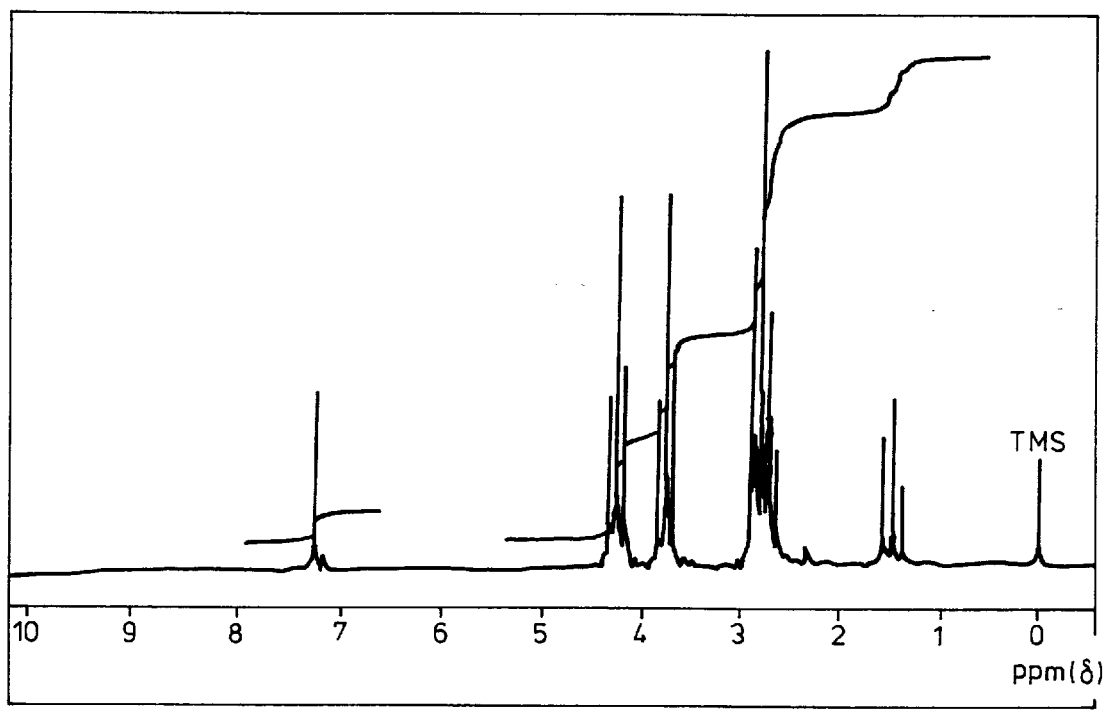
FIGS. 1 to 10 are $^1$H-NMR charts for the respective compounds obtained in Examples 1 to 10.

This invention will be detailed below.

The sulfur-containing O-(meth)acrylate compound of this invention represented by formula (1) can be prepared from the thiol compound represented by formula (2). Specifically, the compound of formula (1) can be prepared by ditihoacetalization, thioesterification or thiourethanization of the thiol compound with a compound having a functional group capable of reacting with the mercapto group of the thiol compound, such as aldehydes, carboxylic acids and isocyanates, and then dehydrohalogenation of the product.

The thiol compound of this invention represented by formula (2) can be prepared as follows. 2-Mercaptoethanol, 3-mercaptopropanol or the like is heated at 10 to 200° C. with a compound such as 3-chloropropionic acid, 3-bromopropionic acid, 3-chloro-2-methylpropionic acid and 3-bromo-2-methylpropionic acid, in the presence of a catalyst such as p-toluenesulfonic acid, sulfuric acid and hydrochloric acid, in a solvent, while removing water generated, that is, via a dehydro-esterification. Alternatively, in the light of stability of the starting material such as 2-mercaptoethanol or 3-mercaptopropanol, the dehydro-esterification may be conducted with mild heating of the reaction system under a reduced pressure of 20 to 400 mmHg to give the thiol.

Using the thiol compound of this invention, it is possible to introduce a sulfur atom into a product molecule to further improve its refractive index. Furthermore, the thiol compound of this invention can be derived to an O-(meth)acrylate compound after reaction in its mercapto group and then dehydrohalogenation, that is, it can easily react with a compound having a functional group capable of reacting with a mercapto group such as aldehydes, carboxylic acids and isocyanates to give a desired sulfur-containing O-(meth)acrylate compound with a high purity.

When definition B is

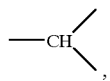

the sulfur-containing O-(meth)acrylate compound of this invention represented by formula (1) can be prepared with a compound having at least one aldehyde group and the thiol compound of formula (2) by a process comprising the following two steps.

First, the compound having at least one aldehyde group is heated with the above thiol compound at 10 to 200° C. in a solvent, in the presence of a catalyst such as p-toluenesulfonic acid, sulfuric acid and hydrochloric acid, while removing water generated, that is, via dehydrodithioacetalization. Next, the mixture was treated with a base at −20 to 60° C. to dehydrohalogenate the product to give the desired (meth)acrylated compound.

The bases used as a hydrogen-halide trap in the latter (meth)acrylation step include, but not limited to, generally-used bases; for example, trialkylamines such as trimethylamine and triethylamine, pyridine, sodium hydroxide and potassium hydroxide.

The compounds having at least one aldehyde group include readily-available aldehyde compounds and those having any of the following structures:

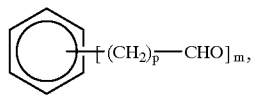

 and

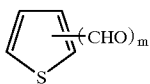

wherein m represents 1 or 2; each ring may be substituted by one or more alkyl, alkylthio or alkoxy groups having 1 or 2 carbon atoms; p and q are 0 or 1, while m is 1 when p is 1.

The specific aldehydes which can be used, include benzaldehyde, 2-methylbenzaldehyde, 3-methylbenzaldehyde, 4-ethylbenzaldehyde, 2,4-dimethylbenzaldehyde, 2,5-dimethylbenzaldehyde, 3,4-dimethylbenzaldehyde, 2,4,5-trimethylbenzaldehyde, 2,4,6-trimethylbenzaldehyde, 2-methoxybenzaldehyde, 3-methoxybenzaldehyde, 4-methoxybenzaldehyde, 2,3-dimethoxybenzaldehyde, 2,4-dimethoxybenzaldehyde, 2,5-dimethoxybenzaldehyde, 3,4-dimethoxybenzaldehyde, 3,5-dimethoxybenzaldehyde, 2-ethoxybenzaldehyde, 3-ethoxybenzaldehyde, 4-ethoxybenzaldehyde, phthalaldehyde, isophthalaldehyde, terephthalaldehyde, 2-methylthiobenzaldehyde, 4-methylthiobenzaldehyde, 4-methylthiomethylbenzaldehyde, phenylacetoaldehyde, 2-thiophenealdehyde, 3-thiophenealdehyde, 3-methyl-2-thiophenealdehyde, 4-methyl-2-thiophenealdehyde, 5-methyl-2-thiophenealdehyde, 5-ethyl-2-thiophenealdehyde, 5-methylthiothiophene-2-aldehyde, 2,3-thiophenedialdehyde, 2,5-thiophenedialdehyde, 1-naphthoaldehyde, 2-naphthoaldehyde, 1,2-naphthalenedialdehyde and 2,3-naphthalenedialdehyde.

Each sulfur-containing O-(meth)acrylate of this invention represented by formula (1) has a main chain with the same structure and thus has an essentially equal distance between intramolecular crosslinking points. Therefore, it is possible to select resins with different optical properties by altering an aldehyde compound constituting a mother skeleton, without largely varying thermal properties, mechanical properties, or the like of a resin obtained.

Similarly, when definition B is

the sulfur-containing O-(meth)acrylate compound of this invention represented by formula (1) can be prepared with a sulfur-containing carboxylic acid compound having at least two carboxyl groups in its molecule and the thiol compound of formula (2) by a process comprising two steps of thio-esterification and dehydrohalogenation.

When definition B is

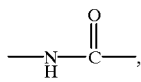

the sulfur-containing O-(meth)acrylate compound of this invention represented by formula (1) can be prepared with a compound having two isocyanate groups in its molecule and the thiol compound of formula (2) by a process comprising two steps of thiourethanization and dehydrohalogenation.

When definition B is

the sulfur-containing carboxylic acid constituting a mother skeleton for the sulfur-containing O-(meth)acrylate compound is a readily available carboxylic acid, having any of the following structures:

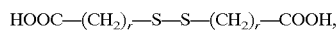
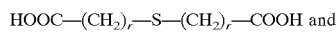
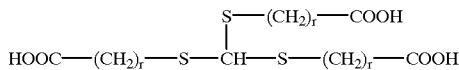

wherein r and s are an integer from 1 to 3.

The specific acids which can be used, include thiodiglycolic acid, thiodipropionic acid, 4,4-thiodibutanoic acid, dithiodiglycolic acid, dithiodipropionic acid, 4,4-dithiodibutanoic acid, methylene-bis(thioglycolic acid), methylenebis(thiopropionic acid), methylenebis(thiobutanoic acid), ethylenebis(thioglycolic acid), ethylenebis(thiopropionic acid), ethylenebis-(thiobutanoic acid), methinetris(thioglycolic acid), methinetris(thiopropionic acid), and methinetris-(thiobutanoic acid). These sulfur-containing O-(meth)acrylate compounds are more hydrophilic because of having a number of intramolecular ester bonds, which is expected to give a lens improved in tintability.

When definition B is

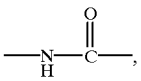

, the isocyanate compound constituting a mother skeleton for the sulfur-containing O-(meth)acrylate compound has any of the following structures:

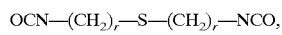
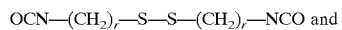

wherein r and s are an integer from 1 to 3.

The specific compounds which can be used, include diisocyanatomethyl sulfide, diisocyanatoethyl sulfide, diisocyanatopropyl sulfide, diisocyanatomethyl disulfide, diisocyanatoethyl disulfide, diisocyanatopropyl disulfide, bis (isocyanatomethylthio)methane, bis(isocyanatoethylthio) methane and bis(isocyanatopropylthio)methane. Thus obtained sulfur-containing O-(meth)acrylate compounds are expected to have improvement in a refractive index and resin strength such as impact resistance because of having an intramolecular thiourethane bond.

In these reactions, if necessary, organic solvents can be used. The solvents which can be used, are, but not limited to, those which do not react with starting materials used in the reactions. Such organic solvents include aliphatic and aromatic hydrocarbons and halogenated hydrocarbons such as benzene, toluene, xylenes, hexane, heptane, petroleumether, chloroform, methylene chlorides and ethylene chlorides; ethers such as diethylether, dioxane and tetrahydrofuran; ketones such as acetone and methyl ethyl ketone; and N,N-dimethylformamide. The solvents used are selected based on materials used, type of the reaction or the like, as appropriate.

These thiol, aldehyde, sulfur-containing carboxylic acid and isocyanate compounds may have been, if necessary, purified by distillation or the like.

The sulfur-containing O-(meth)acrylate compounds prepared by these processes are improved in stability as a monomer, are relatively hard to gel and are more easily handled in comparison with thio(meth)acrylate compounds.

The optical resin compositions of this invention include those comprising the sulfur-containing O-(meth)acrylate compound of this invention, and those comprising the sulfur-containing O-(meth)acrylate compound of this invention and at least one of monomers co-polymerizable with the acrylate of this invention, or polythiol compounds. For the composition comprising monomers other than the acrylate of this invention or polythiol compounds, the sulfur-containing O-(meth)acrylate compound of this invention is contained in more than 20% by weight, preferably more than 40% by weight, more preferably more than 60% by weight, to the total amount of the sulfur-containing O-(meth)acrylate compound and the other monomers or the polythiol compounds.

The monomers co-polymerizable with the acrylate of this invention or the polythiol compounds may be selected, based on their purposes such as, but not limited to, adjustment of optical properties including a refractive index, various physical properties including impact resistance and specific gravity and parameters relevant to handling including viscosity of the monomer. The co-polymerizable monomers or the polythiol compounds may be used solely or in combination of two or more components.

The co-polymerizable monomers include (meth)acrylate compounds such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylates, polyethylene glycol dimethacrylates, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4-acryloxyethoxyphenyl)sulfone, 1,1-bis(4-methacryloxyethoxyphenyl)sulfone, 1,1-bis(4-acryloxydiethoxyphenyl)sulfone, 1,1-bis(4-methacryloxydiethoxyphenyl)sulfone, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methylthio acrylate, methylthio methacrylate, phenylthio acrylate, benzylthio methacrylate, xylylenedithiol diacrylates, xylylenedithiol dimethacrylates, mercaptoethyl sulfide diacrylate and mercaptoethyl sulfide dimethacrylate; allyl compounds such as allyl glycidyl ether, diallyl phthalate, diallyl terephthalate, diallyl isophthalate, diallyl carbonate and diethylene glycol bis(allylcarbonate); vinyl compounds such as styrene, chlorostyrenes, methylstyrenes, bromostyrenes, dibromostyrene, divinylbenzenes and 3,9-divinylspiro-bi(m-dioxane); and diisopropenylbenzene.

The polythiol compounds include 1,2-ethanedithiol, 1,3-propanedithiol, 1,2,3-propanetrithiol, 2,3-dimercapto-1-propanol, diethylene glycol bis(2-mercapto-acetate), diethylene glycol bis(3-mercaptopropionate), trimethylolpropane bis(2-mercaptoacetate), trimethylol-propane bis(3-mercaptopropionate), pentaerythritol tetrakis(2-mercaptoacetate), pentaerythritol tetrakis(3-mercaptopropionate), 1,2-dimercaptobenzene, 1,3-dimercaptobenzene, 1,4-dimercaptobenzene, 1,2-bis(mercaptomethyl)benzene, 1,3-bis(mercaptomethyl) benzene, 1,4-bis(mercaptomethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercapto-methyl)benzene, 1,3,5-tris(mercaptomethyl)benzene, 4,4-thiobisbenzenethiol, bis(2-mercaptoethyl) sulfide; bis(2-mercaptoethylthio)methane, 1,2-bis(2-mercaptoethylthio) ethane, 1,3-bis(2-mercaptoethylthio)propane, 1,2,3-tris(2-mercaptoethylthio) propane, tetrakis(2-mercapto-ethylthiomethyl)methane, 1,2-bis(2-mercaptoethylthio)-3-mercaptopropane, 4,8-bis(mercaptomethyl)-3,6,9-trithia-1,11-undecanedithiol, 2,5-dimercapto-1,4-dithiane, 2,5-dimercaptomethyl-1,4-dithiane and 2,5-dimercaptomethyl-2,5-dimethyl-1,4-dithiane. The co-polymerizable monomer is preferably the compound represented by the following formula (3):

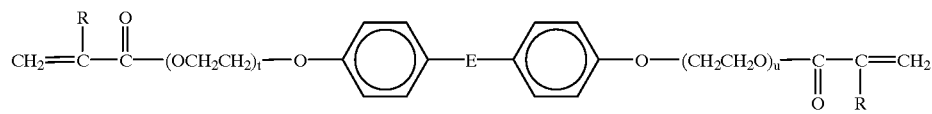

(3)

wherein R represents a hydrogen atom or methyl group; t and u represent an integer from 0 to 4; and E represents —CH$_2$—, —C(CH$_3$)$_2$—, —S— or —SO$_2$—.

The optical resin of this invention is prepared by polymerizing the optical resin composition of this invention; specifically, by polymerizing solely the sulfur-containing O-(meth)acrylate compound of this invention or co-polymerizing the sulfur-containing O-(meth)acrylate compound of this invention and another co-polymerizable monomer or the polythiol compound.

A polymerization procedure for providing the optical resin of this invention may be, but not limited to, any of the known radical polymerization methods.

The polymerization may be initiated by using a radical initiator such as a variety of peroxides and azo compounds, or by irradiation of UV rays, visible light, α-ray, β-ray, γ-ray, electron ray or the like or combination thereof.

The typical radical initiators which can be used, include peroxides such as benzoyl peroxide, dicumyl peroxide, lauroyl peroxide, di-t-butylperoxy azelate, t-butyl-peroxy-2-ethyl hexanoate, t-butylperoxy laurate, t-butylperoxy benzoate, t-butylperoxy-3,5,5-trimethyl-hexanoate, t-butylperoxy acetate, bis(4-t-butyl-cyclohexyl)peroxy dicarbonate and t-butylperoxy isopropyl carbonate, and azo compounds such as azobisisobutyronitrile, which may be used solely or in combination of two or more.

For initiation of polymerization by irradiation of UV-rays or the like, the known photo-initiators may be also used. The typical photo-initiators include benzophenone, 4,4-diethylaminobenzophenone, 1-hydroxycyclohexyl phenyl ketone, 2,2-dimethoxy-2-phenylacetophenone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenylpropan-1-one, 2,4,6-trimethylbenzoyldiphenylphosphine oxide and bisacylphosphine oxide, which may be used solely or in combination of two or more, or in combination with any of the above radical initiators.

The typical polymerization processes for preparing the optical resins (e.g., a plastic lens) of this invention include casting polymerization. Specifically, the optical resin composition of this invention containing a radical- or photo-initiator or both, which may be referred to as a monomer mixture, is poured between molds held by a gasket, tapes or the like, during which some treatments such as defoaming may be conducted.

Then, it is subject to irradiation of UV rays or the like, or to heating in an oven, or in combination thereof, and then a polymerization product may be released.

A polymerization method or polymerization conditions for preparing the optical resin of this invention cannot be generalized since they depend on the amounts and types of reagents such as initiators as well as types and proportions of monomers.

For example, for irradiation of UV rays or the like, treatments such as cooling may be applied to prevent a monomer mixture from being overheated, or a wavelength cut filter or the like capable of cutting rays below a particular wavelength may be used for irradiation with only rays within a wavelength band necessary for the desired polymerization. For heating in an oven, temperature may be controlled to select an optimal thermal condition. In general, the temperature may be slowly raised from a lower one to a predetermined one which is maintained to complete the polymerization. The polymerization period cannot be generalized since it depends on the amounts and types of reagents such as initiators as well as types and proportions of monomers.

Generally, it is possible to shorten the polymerization period by UV irradiation or the like.

For molding the resin of this invention, a variety of substances such as chain extenders, crosslinking agents, photostabilizers, U absorbers, antioxidants, anti-coloring agents, dyes, perfumes and fillers, may be added, depending on a purpose, as in the known molding methods.

The molded resin which has been released may be, if necessary, subjected to any post-treatment such as annealing.

An optical resin obtained from the sulfur-containing O-(meth)acrylate of this invention has characteristics, that is, it has a high refractive index and is low-dispersing, and is excellent in thermal resistance, weather resistance and, in particular, impact resistance, and that it generates less unpleasant odor during processing. Furthermore, the resin of this invention can be formed as a molded resin which may be in various forms by altering a mold in the casting polymerization, and can be, therefore, used as an optical device such as lenses for eyeglasses and cameras, as well as a transparent resin for a variety of applications. In particular, it is suitable for an optical device such as lenses for eyeglasses and cameras.

Furthermore, a lens prepared with the optical resin of this invention may be, if necessary, subjected to physical or chemical treatments such as surface abrasion, antistatic treatment, hard coating, anti-reflection coating and dyeing, for improvements such as prevention of reflection; improvement in hardness, abrasion resistance or chemical resistance; and impartation of antifogging or ornamental characteristics.

This invention will be specifically described by the following examples. The properties relevant to performance of an optical resin obtained, that is, a refractive index ($n_D$), Abbe number (v), a specific gravity, impact resistance, odor during abrasion and appearance are evaluated as follows.

(1) A refractive index (nd) and Abbe number ($v_d$) were measured at 20° C. using a Pulfrich refractometer.

(2) Appearance was visually observed.

(3) Impact resistance was evaluated by dropping a steel ball with different weights on the center of a lens obtained from the height of 127 cm. The result was represented by the weight of the heaviest steel ball which did not crack or break the lens.

(4) Odor during abrasion was rated according to the following criteria by detecting whether unpleasant sulfur odor was generated during cutting and abrasion of an edge of a lens with an edger. The evaluation is as follows:

○; No unpleasant sulfur odor

Δ; Slight sulfur odor x; Unpleasant sulfur odor

EXAMPLE 1

To a reaction flask equipped with a stirring rod, a thermometer and a Dean-Stark trap with a condenser were placed 65.1 g (0.60mol) of 3-chloropropionic acid, 56.3 g (0.72 mol) of 2-mercaptoethanol, 400 ml of toluene and 3.0 g of p-toluenesulfonic acid, and the mixture was then heated for 9 hours under a controlled pressure between 40 and 70 mmHg to maintain reflux at 40° C. to complete dehydroesterification. The organic layer was then washed with 5% aqueous sodium bicarbonate solution and then water (several times).

The organic layer was dried over anhydrous magnesium sulfate and toluene was evaporated under a reduced pressure, to give 97.7 g (0.58 mol) of 2-mercaptoethyl-3-chloropropionate represented by the following formula, as a colorless liquid.

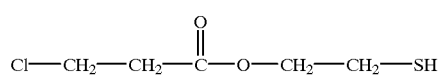

The results of an elemental analysis for the product are shown below.

Composition: C₅H₉ClO₂S

|  | C | H | S | Cl |
|---|---|---|---|---|
| Observed (%) | 35.4 | 5.3 | 19.3 | 21.1 |
| Calculated (%) | 35.6 | 5.4 | 19.0 | 21.0 |

Its ¹H-NMR chart is shown in FIG. 1 (solvent: CDCl₃, reference: tetramethylsilane).

EXAMPLE 2

To a reaction flask equipped with a stirring rod, a thermometer and a Dean-Stark trap with a condenser were placed 21.2 g (0.20 mol) of benzaldehyde, 70.8 g (0.42 mol) of 2-mercaptoethyl 3-chloropropionate, 0.3 g of p-toluenesulfonic acid and 300 ml of toluene, and the mixture was then heated for 2 hours under a controlled pressure between 80 and 110 mmHg to maintain reflux at 50° C. to complete dithioacetalization. After cooling, the organic layer was then washed with water (once), 5% aqueous sodium bicarbonate solution (once) and then water (several times).

The organic layer was dried over anhydrous magnesium sulfate and toluene was evaporated under a reduced pressure, to give 82.1 g (0.19 mol) of a colorless liquid.

The liquid was dissolved in 200 ml of acetone, and the solution was placed into a reaction flask equipped with a stirring rod, a thermometer and a dropping funnel. The mixture was cooled to below 10° C., and with stirring, 43.0 g (0.42 mol) of triethylamine was slowly added, after which the mixture was stirred for 10 hours at 25° C.

To the mixture were then added 200 ml of toluene and 200 ml of water to extract the reaction product into the organic layer and then the two phases where separated. The organic layer was washed with diluted hydrochloric acid, diluted aqueous sodium bicarbonate solution and then water. The organic layer was dried over anhydrous magnesium sulfate and toluene was evaporated under a reduced pressure, to give 66.9 g of the desired sulfur-containing O-acrylate compound represented by the following formula, i.e., bis(2-acryloyloxyethyl)dithioacetal benzene (0.190 mol) as a colorless and transparent material.

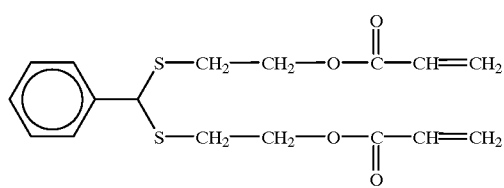

The results of an elemental analysis for the product are shown below.

Composition: C₁₇H₂₀O₄S₂

|  | C | H | S |
|---|---|---|---|
| Observed (%) | 57.8 | 5.8 | 18.4 |
| Calculated (%) | 57.9 | 5.7 | 18.2 |

Figure 2:
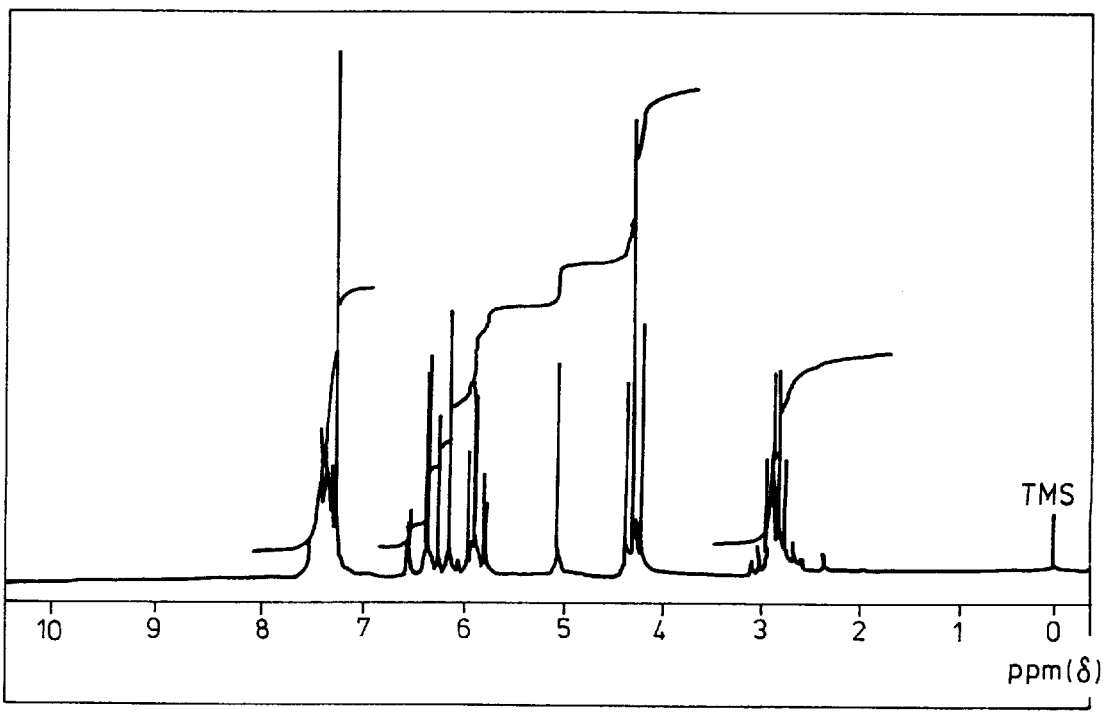

Its ¹H-NMR chart is shown in FIG. 2 (solvent: CDCl₃, reference: tetramethylsilane).

EXAMPLE 3

Dithioacetalization and acrylation reactions were conducted as described in Example 2, except that 21.2 g (0.20 mol) of benzaldehyde was replaced with 30.4g (0.20 mol) of 4-methylthiobenzaldehyde, to give 76.4 g of the sulfur-containing O-acrylate compound represented by the following formula, i.e., 4-methylthiobis(2-acryloyloxyethyl) dithioacetal benzene (0.192 mol) as a colorless and transparent material.

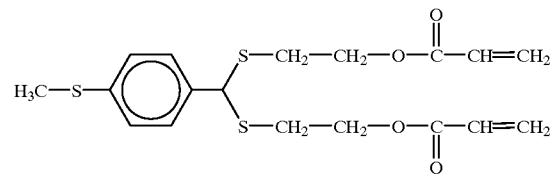

The results of an elemental analysis for the product are shown below.

Composition: C₁₈H₂₂O₄S₃

|  | C | H | S |
|---|---|---|---|
| Observed (%) | 53.9 | 5.8 | 24.4 |
| Calculated (%) | 54.2 | 5.6 | 24.1 |

Figure 3:
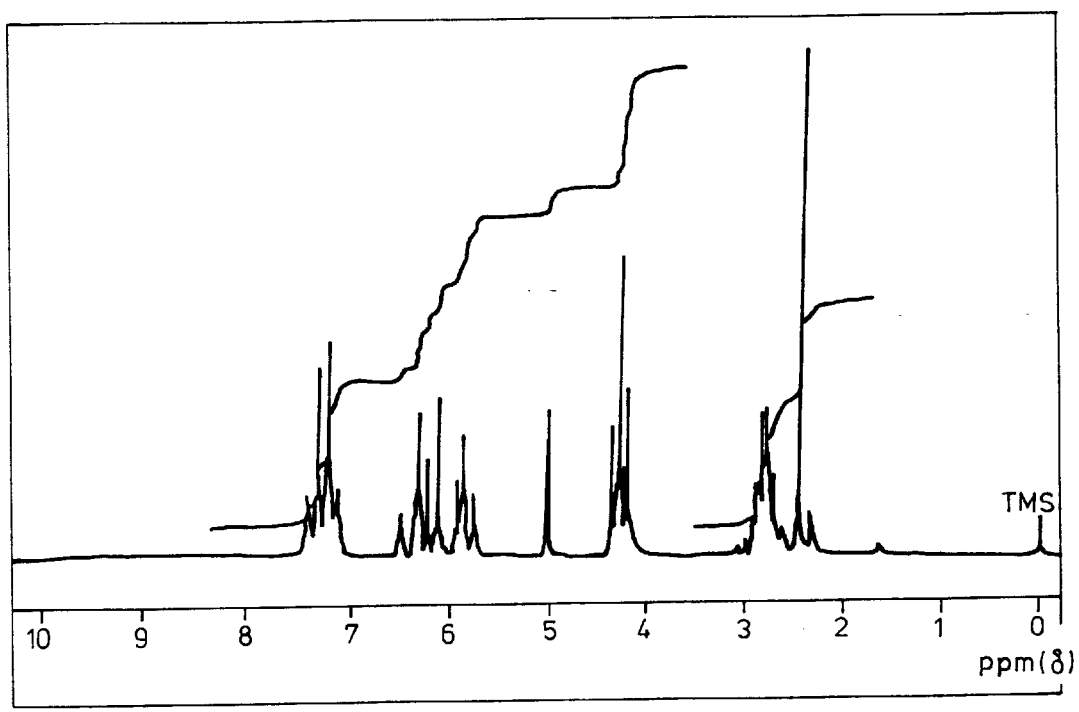

Its ¹H-NMR chart is shown in FIG. 3 (solvent: CDCl₃, reference: tetramethylsilane).

EXAMPLE 4

Dithioacetalization and acrylation reactions were conducted as described in Example 2, except that 21.2 g (0.20 mol) of benzaldehyde was replaced with 31.2g (0.20 mol) of 1-naphthoaldehyde, to give 78.3 g of the sulfur-containing O-acrylate compound represented by the following formula, i.e., 1-bis(2-acryloyloxyethyl)dithioacetal naphthalene (0.195 mol) as a colorless and transparent material.

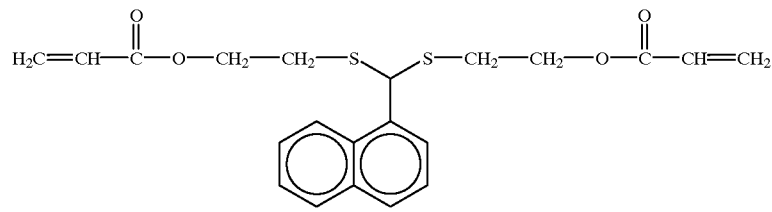

The results of an elemental analysis for the product are shown below.

Composition: $C_{21}H_{22}O_4S_2$

|  | C | H | S |
|---|---|---|---|
| Observed (%) | 62.6 | 5.6 | 16.1 |
| Calculated (%) | 62.7 | 5.5 | 15.9 |

Figure 4:
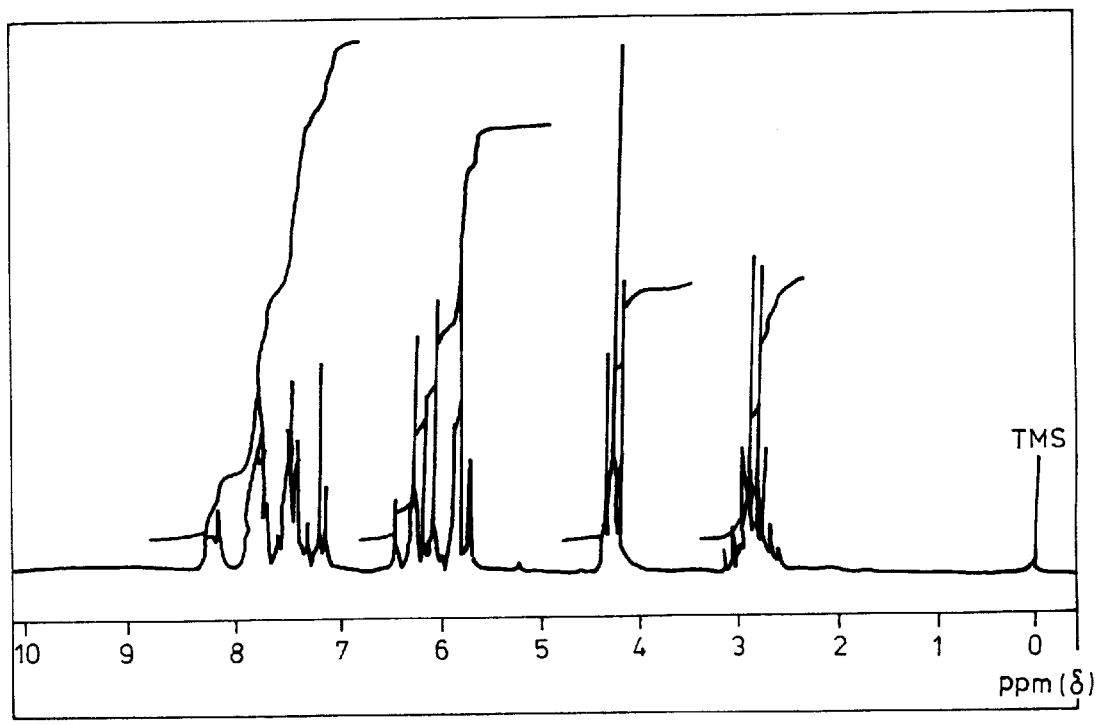

Its $^1$H-NMR chart is shown in FIG. 4 (solvent: CDCl$_3$, reference: tetramethylsilane).

EXAMPLE 5

Dithioacetalization and acrylation reactions were conducted as described in Example 2, except that 21.2 g (0.20 mol) of benzaldehyde was replaced with 22.4g (0.20 mol) of 2-thiophenealdehyde, to give 54.1 g of the sulfur-containing O-acrylate compound represented by the following formula, i.e., 2-bis(2-acryloyloxyethyl)dithioacetal thiophene (0.151 mol) as a colorless and transparent material.

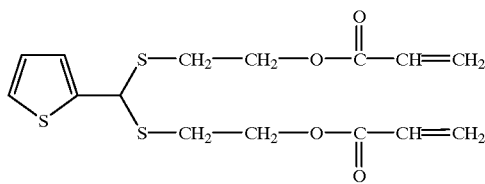

The results of an elemental analysis for the product are shown below.

Composition: $C_{15}H_{18}O_4S_3$

|  | C | H | S |
|---|---|---|---|
| Observed (%) | 50.4 | 5.0 | 26.7 |
| Calculated (%) | 50.3 | 5.1 | 26.8 |

Figure 5:
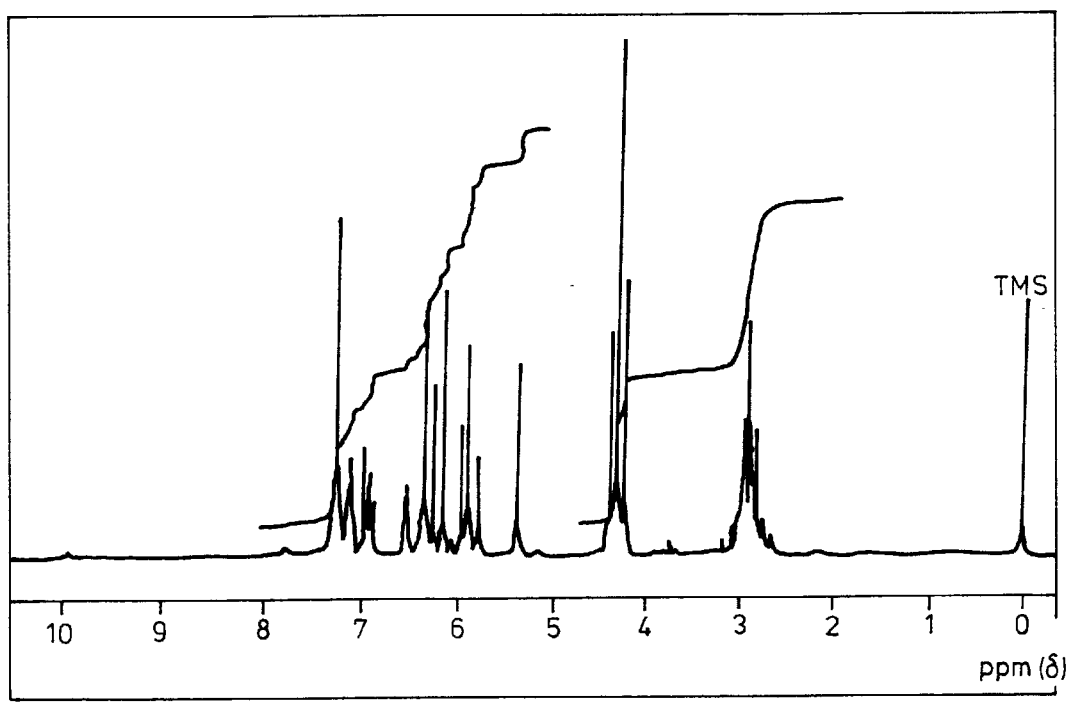

Its $^1$H-NMR chart is shown in FIG. 5 (solvent: CDCl$_3$, reference: tetramethylsilane).

EXAMPLE 6

Dithioacetalization and acrylation reactions were conducted as described in Example 2, except that 21.2 g (0.20 mol) of benzaldehyde was replaced with 24.0 g (0.20 mol) of phenylacetoaldehyde, to give 65.2 g of the sulfur-containing O-acrylate compound represented by the following formula, i.e., phenylmethylenebis(2-acryloyloxyethyl) dithioacetal (0.178 mol) as a colorless and transparent material.

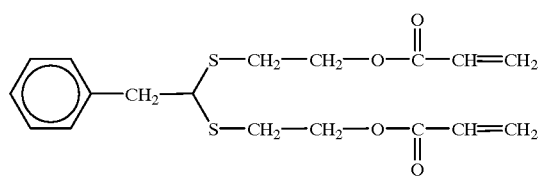

The results of an elemental analysis for the product are shown below.

Composition: $C_{16}H_{22}O_4S_2$

|  | C | H | S |
|---|---|---|---|
| Observed (%) | 59.3 | 6.0 | 17.7 |
| Calculated (%) | 59.0 | 6.1 | 17.5 |

Figure 6:
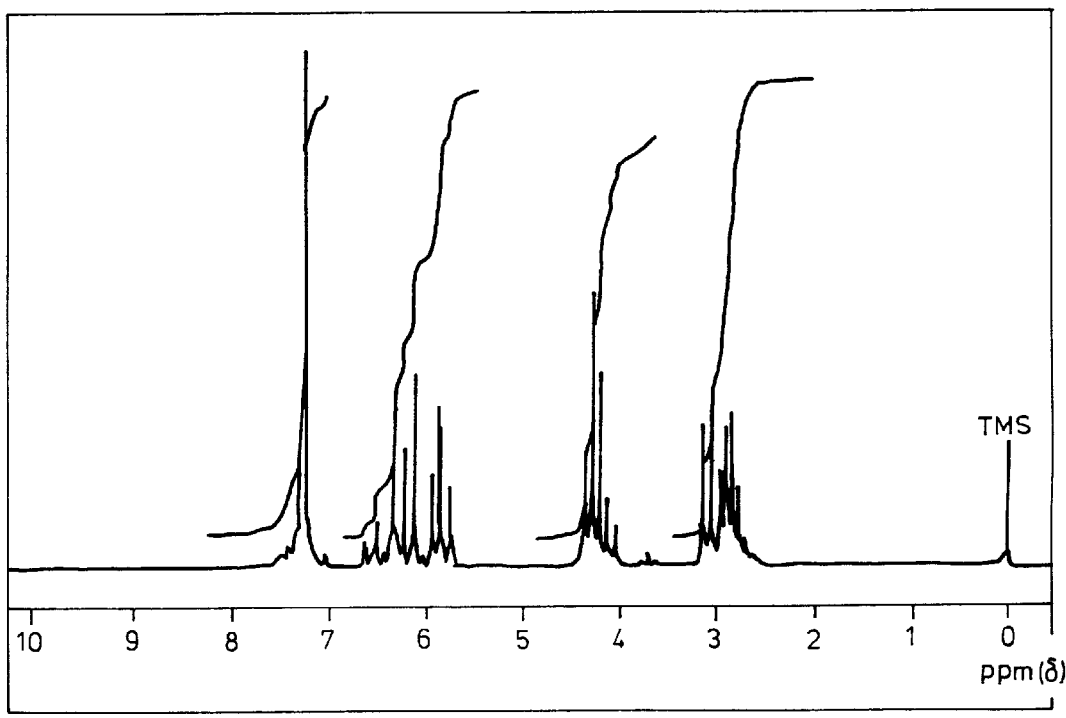

Its $^1$H-NMR chart is shown in FIG. 6 (solvent: CDCl$_3$, reference: tetramethylsilane).

EXAMPLE 7

To a reaction flask equipped with a stirring rod, a thermometer and a dropping funnel were placed 39.3 g (0.20 mol) of methylenebis(thioglycolic acid), 81.0 g (0.48 mol) of 2-mercaptoethyl-3-chloropropionate, 0.1 g of dimethylaminopyridine and 400 ml of chloroform. With stirring, to the mixture was slowly added a solution of 90.8 g (0.44 mol) of dicyclohexylcarbodiimide in 100 ml of chloroform on a water bath, after which the mixture was stirred at 25° C. for additional 15 hours. Excessive dicyclohexylcarbodiimide was quenched with acetic acid, and then urea formed was removed by vacuum filtration. After evaporation of chloroform under a reduced pressure, the residual material was dissolved in 300 ml of toluene. The organic layer was washed with 5% aqueous sodium bicarbonate solution and then water and dried over anhydrous magnesium sulfate. Toluene was evaporated under a reduced pressure to give 88.6 g (0.18 mol) of colorless liquid.

The liquid was dissolved in 300 ml of acetone and placed in a reaction flask equipped with a stirring rod, a thermometer and a dropping funnel. Cooling to below 10° C., to the mixture was slowly added 37.8 g (0.37 mol) of triethylamine, after which the mixture was stirred at 25° C. for additional 10 hours.

Then, to the mixture were 400 ml of toluene and 300 ml of water, and the reaction product was extracted into the organic layer. After separation of the two phases, the organic layer was washed with diluted hydrochloric acid, diluted aqueous sodium bicarbonate solution and water. The organic layer was dried over anhydrous magnesium sulfate, and toluene was evaporated under a reduced pressure, to give 59.2 g of the desired sulfur-containing O-acrylate compound, i.e., methylenebis(acryloyloxyethylthio thioglycolate) (0.14 mol) as a colorless and transparent material.

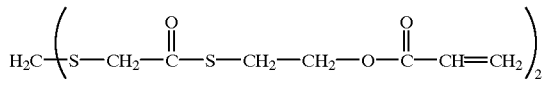

The results of an elemental analysis for the product are shown below.

Composition: $C_{15}H_{20}O_6S_4$

|  | C | H | S |
|---|---|---|---|
| Observed (%) | 42.3 | 5.0 | 29.7 |
| Calculated (%) | 42.4 | 4.8 | 30.2 |

Figure 7:
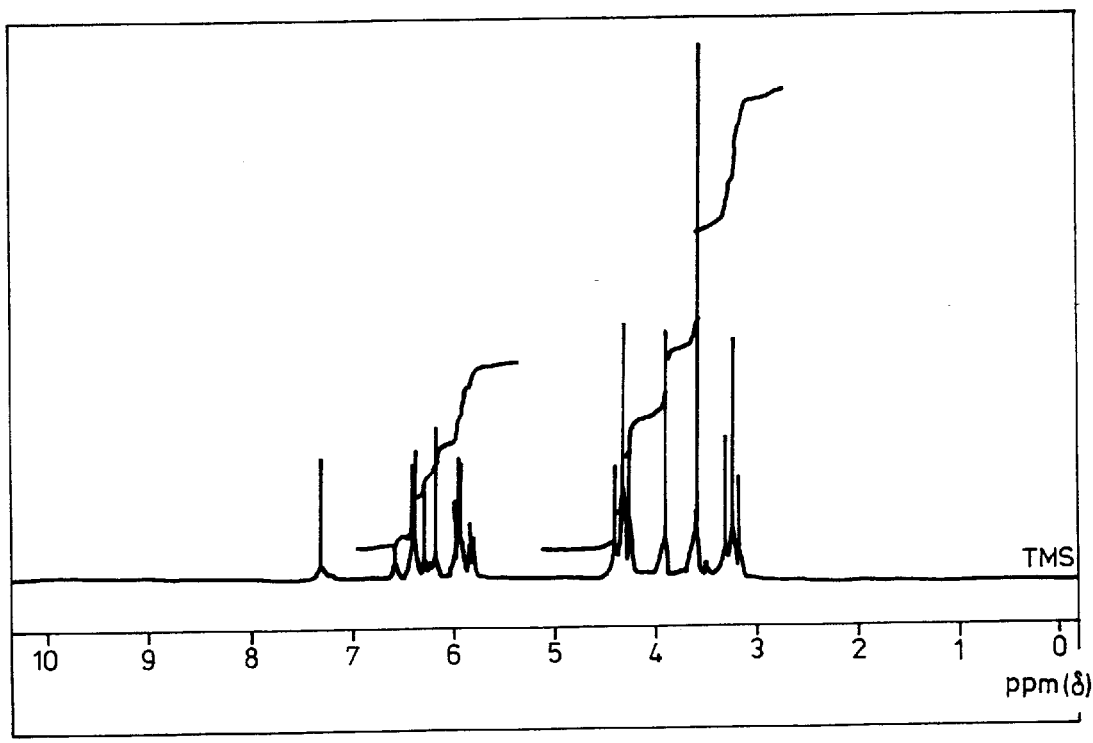

Its $^1$H-NMR chart is shown in FIG. 7 (solvent: CDCl$_3$, reference: tetramethylsilane).

EXAMPLE 8

Dehydroesterification and acrylation reactions were conducted as described in Example 7, except that 39.3 g (0.20 mol) of methylenebis(thioglycolic acid) of Example 7 was replaced with 30.0 g (0.20mol) of thiodiglycolic acid, to give 52.7 g of the sulfur-containing O-acrylate compound represented by the following formula, i.e., bis(acryloyloxyethylthio)-thiodiglycolate (0.14 mol) as a colorless and transparent material.

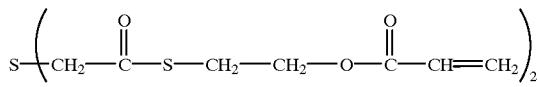

The results of an elemental analysis for the product are shown below.

Composition: $C_{14}H_{18}O_6S_3$

|  | C | H | S |
|---|---|---|---|
| Observed (%) | 44.5 | 4.7 | 25.7 |
| Calculated (%) | 44.4 | 4.8 | 25.4 |

Figure 8:
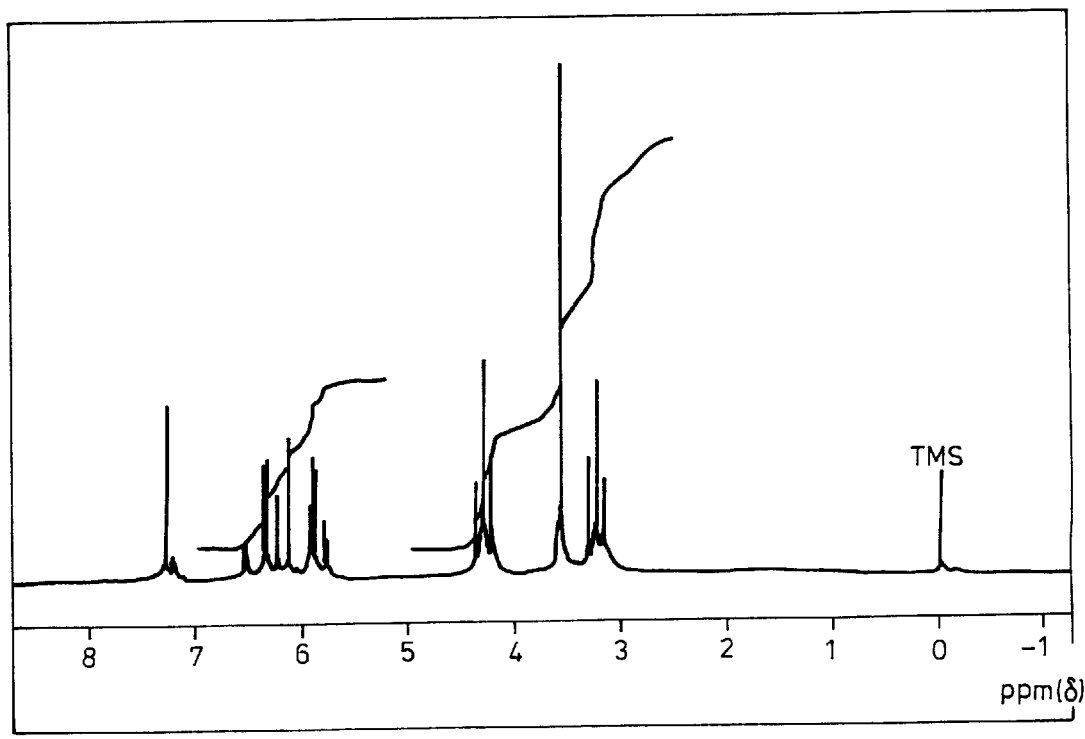

Its $^1$H-NMR chart is shown in FIG. 8 (solvent: $CDCl_3$, reference: tetramethylsilane).

EXAMPLE 9

Dehydroesterification and acrylation reactions were conducted as described in Example 7, except that 39.3 g (0.20 mol) of methylenebis(thioglycolic acid) of Example 7 was replaced with 57.3 g (0.20 mol) of methinetris(thioglycolic acid), and the amounts of the materials used, i.e., 2-mercaptoethyl-3-chloropropionate, dicyclohexylcarbodiimide and triethylamine were changed to 0.72 mol, 0.66 mol and 0.59 mol, respectively, to give 100.6 g of the sulfur-containing 0-acrylate compound represented by the following formula, i.e., methinetris(acryloyloxyethylthio thioglycolate) (0.16 mol) as a colorless and transparent material.

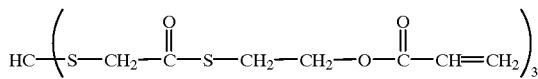

The results of an elemental analysis for the product are shown below.

Composition: $C_{22}H_{28}O_9S_6$

|  | C | H | S |
|---|---|---|---|
| Observed (%) | 42.3 | 4.4 | 30.3 |
| Calculated (%) | 42.0 | 4.5 | 30.6 |

Figure 9:
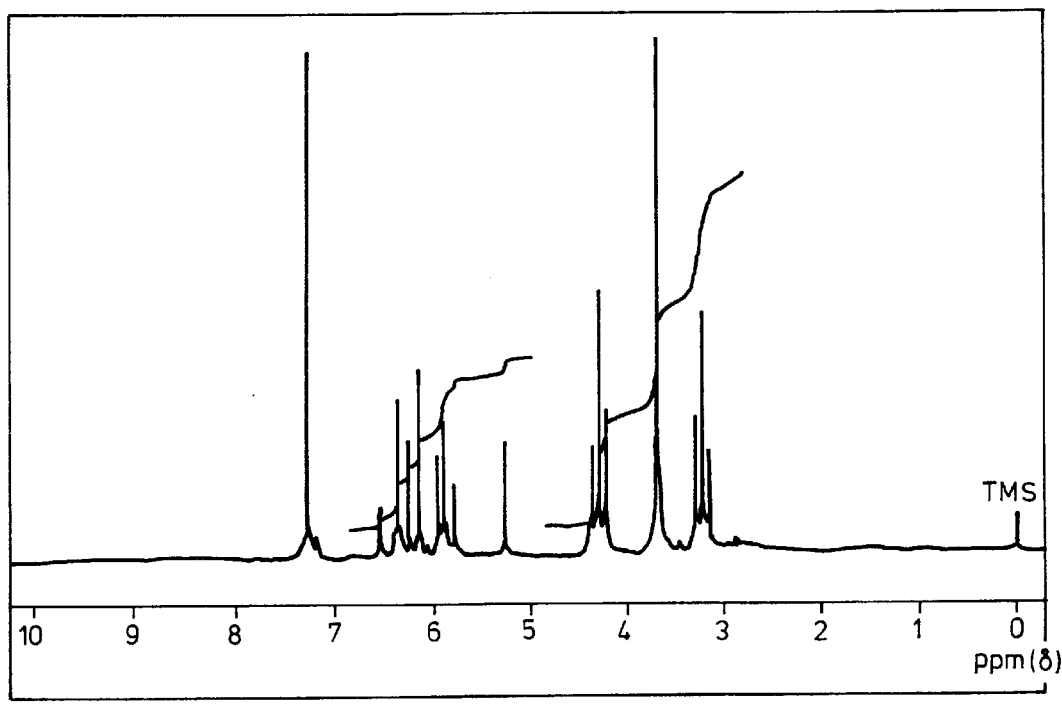

Its $^1$H-NMR chart is shown in FIG. 9 (solvent: $CDCl_3$, reference: tetramethylsilane).

EXAMPLE 10

To a reaction flask equipped with a stirring rod, a thermometer and a dropping funnel were placed 19.0 g (0.10 mol) of bis(isocyanatomethylthio)methane, 15 mg of dimethyltin dichloride and 100 ml of toluene. With stirring, to the mixture was slowly added 33.7 g (0.20 mol) of 2-mercaptoethyl-3-chloropropionate on a water bath, after which the mixture was stirred for 2 hours at the same temperature and then for 2 hours at 50° C. After cooling, crystals generated were filtered, washed and dried, to give 42.5 g (0.08 mol) of white crystals.

The crystals were dissolved in 200 ml of acetone and placed in a reaction flask equipped with a stirring rod, a thermometer and a dropping funnel. To the solution was slowly added 17.1 g (0.17 mol) of triethylamine, after which the mixture was stirred at 25° C. for additional 10 hours.

Then, to the mixture were 200 ml of toluene and 200 ml of water, and the reaction product was extracted into the organic layer. After separation of the two phases, the organic layer was washed with diluted hydrochloric acid, diluted aqueous sodium bicarbonate solution and water. The organic layer was dried over anhydrous magnesium sulfate, and toluene was evaporated under a reduced pressure, to give 29.7 g of the desired sulfur-containing O-acrylate compound (0.065 mol) as white crystals.

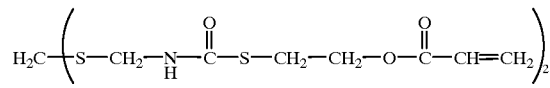

The results of an elemental analysis for the product are shown below.

Composition: $C_{15}H_{22}N_2O_5S_4$

|  | C | H | N | S |
|---|---|---|---|---|
| Observed (%) | 39.8 | 5.1 | 6.0 | 28.5 |
| Calculated (%) | 39.6 | 4.9 | 6.2 | 28.2 |

Figure 10:
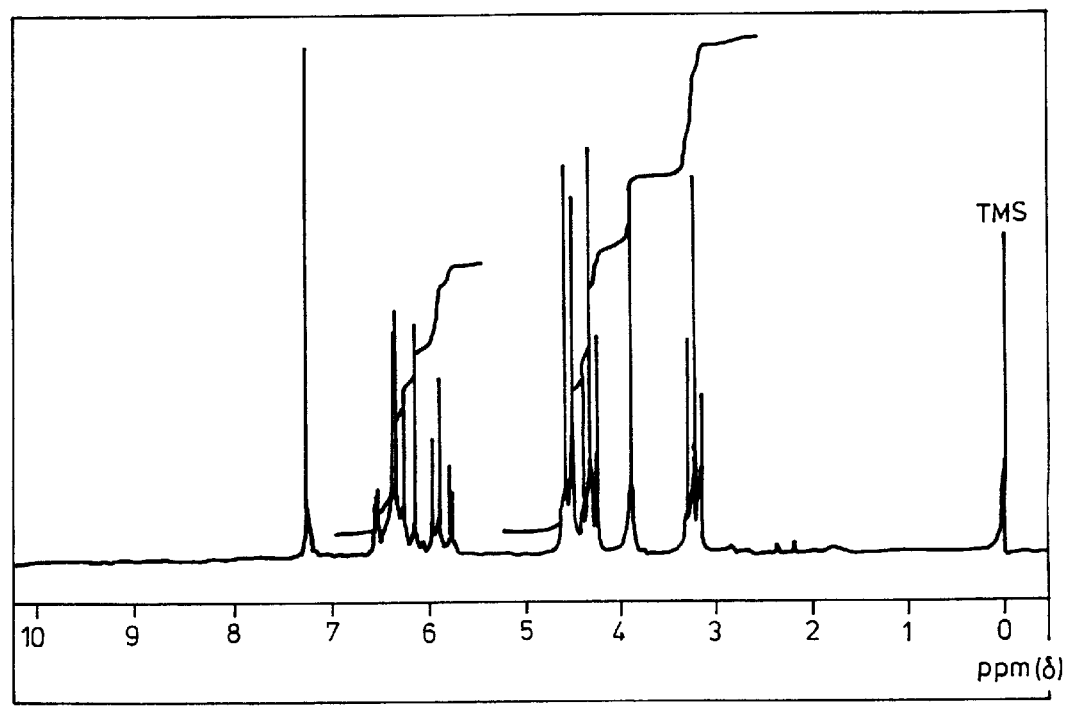

Its $^1$H-NMR chart is shown in FIG. 10 (solvent: $CDCl_3$, reference: tetramethylsilane).

EXAMPLES 11 to 19

To 50 g of each product of Examples 2 to 10 was added 50 to 100 mg of $^2$-hydroxy-2-methyl-1-phenylpropan-1-one as a photoinitiator, and the mixture was thoroughly mixed. After fully defoaming, the mixture was poured into a mold consisting of glass templates and a gasket. The mold was irradiated with UV rays for 10 to 60 sec., and was then heated at 120° C. for 1 hour, to polymerize the composition. After polymerization, it was slowly cooled and the molding product was removed from the mold. The physical properties of the molding products, i.e., lenses, are shown in Table 1.

TABLE 1

| | Monomer | Appearance | Refractive Index | Abbe Number |
|---|---|---|---|---|
| Example 11 | Compd. of Ex. 2 | CL/TR* | 1.600 | 36.5 |
| Example 12 | Compd. of Ex. 3 | CL/TR | 1.624 | 30.4 |
| Example 13 | Compd. of Ex. 4 | CL/TR | 1.637 | 27.5 |
| Example 14 | Compd. of Ex. 5 | CL/TR | 1.609 | 35.8 |
| Example 15 | Compd. of Ex. 6 | CL/TR | 1.600 | 34.6 |
| Example 16 | Compd. of Ex. 7 | CL/TR | 1.602 | 38.5 |
| Example 17 | Compd. of Ex. 8 | CL/TR | 1.589 | 40.7 |
| Example 18 | Compd. of Ex. 9 | CL/TR | 1.606 | 38.2 |
| Example 19 | Compd. of Ex. 10 | CL/TR | 1.632 | 37.5 |

*CL/TR: Colorless and transparent

EXAMPLE 20

To 35 g of bis(2-acryloyloxyethyl)dithioacetal benzene obtained in Example 2 were added 15 g of bis(4-acryloxydiethoxyphenyl)methane and 50 mg of 2-hydroxy-2-methyl-1-phenylpropan-1-one as a photoinitiator, and the mixture was thoroughly mixed. After fully defoaming, the composition was poured into a mold consisting of glass templates and tapes.

The mold was irradiated with UV rays for 10 sec., and was then heated at 120° C. for 1 hour, to polymerize the composition. After polymerization, it was slowly cooled and the molding product was removed from the molds. The physical properties of the molding products, i.e., lenses, are shown in Table 2.

EXAMPLES 21 to 26

The procedure as described in Example 20 was conducted, except that the monomer compositions listed in Table 2 were used, to give plastic lenses, whose evaluation results are shown in Table 2 together with those of Example 20.

The results in Table 2 indicate that the plastic lenses of Examples 20 to 26 were colorless and transparent; had a good balance among a refractive index ($n_d$), Abbe number ($v_d$) and a specific gravity; were excellent in impact resistance; and generated no unpleasant odor during abrasion of the resins.

COMPARATIVE EXAMPLES 1 to 3

The procedure as described in Example 20 was conducted, except that the monomer compositions listed in Table 2 were used, to give plastic lenses, whose evaluation results are shown in Table 2 together with those of Examples 20 to 26.

The results in Table 2 indicate that the plastic lenses of Comparative Examples had lower impact resistance than those of Examples 20 to 26, and generated sulfur odor during abrasion of the resins.

TABLE 2

|  | Portions of monomers (% by weight) |  | $n_d$ | $v_d$ | Spec. Grav. | Impact Resist. | Odor | Appearance |
|---|---|---|---|---|---|---|---|---|
| Example 20 | Compd. of Ex. 2 | 70 | 1.590 | 36 | 1.27 | 117 g | ○ | CL/TR* |
|  | BSFA | 30 |  |  |  |  |  |  |
| Example 21 | Compd. of Ex. 2 | 65 | 1.591 | 36 | 1.27 | 67 g | ○ | CL/TR |
|  | BSFA | 30 |  |  |  |  |  |  |
|  | Divinylbenzene | 5 |  |  |  |  |  |  |
| Example 22 | Compd. of Ex. 3 | 65 | 1.598 | 33 | 1.28 | 67 g | ○ | CL/TR |
|  | BSFA | 30 |  |  |  |  |  |  |
|  | TEGDMA | 5 |  |  |  |  |  |  |
| Example 23 | Compd. of Ex. 4 | 50 | 1.590 | 32 | 1.25 | 117 g | ○ | CL/TR |
|  | BSFA | 50 |  |  |  |  |  |  |
| Example 24 | Compd. of Ex. 6 | 70 | 1.590 | 35 | 1.26 | 67 g | ○ | CL/TR |
|  | BSFA | 30 |  |  |  |  |  |  |
| Example 25 | Compd. of Ex. 7 | 80 | 1.595 | 38 | 1.36 | 117 g | ○ | CL/TR |
|  | BSFA | 20 |  |  |  |  |  |  |
| Example 26 | Compd. of Ex. 10 | 80 | 1.591 | 38 | 1.37 | 117 g | ○ | CL/TR |
|  | BSFA | 15 |  |  |  |  |  |  |
|  | TEGDMA | 5 |  |  |  |  |  |  |
| Comp. Ex. 1 | DTAET | 80 | 1.609 | 42 | 1.29 | 16 g break | x | CL/TR |
|  | DCPA | 20 |  |  |  |  |  |  |
| Comp. Ex. 2 | AETE | 70 | 1.581 | 40 | 1.25 | 16 g break | Δ | CL/TR |
|  | Styrene | 30 |  |  |  |  |  |  |
| Comp. Ex. 3 | XDMET | 80 | 1.588 | 39 | 1.31 | 16 g break | Δ | CL/TR |
|  | BSAM | 20 |  |  |  |  |  |  |

*CL/TR: colorless and transparent
BSFA: bis(4-acryloxydiethoxyphenyl)methane
TEGDMA: tetraethylene glycol dimethacrylate
DTAET: 2,5-bis(acryloxyethylthiomethyl)-1,4-dithiane
AETE: bis(acryloxyethylthio)ethane
XDMET: p-bis(β-methacryloxyethylthio)xylylene
BSAM: 2,2-bis(4-methacryloxydiethoxyphenyl)propane
DCPA: dimethylol tricyclodecane diacrylate

What is claimed is:

1. A sulfur-containing O-(meth)acrylate compound of the following formula (1):

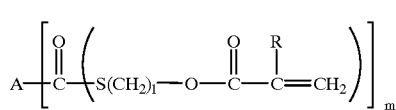

(1)

wherein R represents hydrogen atom or methyl group; l represents an integer from 1 to 3;
m is 2 or 3; A is selected from the following groups:

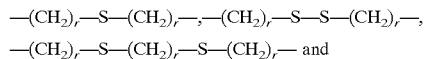

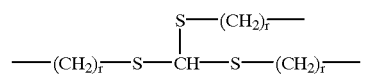

wherein r and s are an integer from 1 to 3.

2. A process for preparation of a sulfur-containing O-(meth)acrylate compound according to claim 1, comprising thioesterification of a thiol compound represented by the following formula (2):

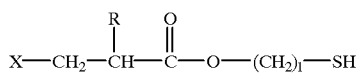

(2)

wherein X represents Cl or Br; R represents hydrogen atom or methyl group; and l represents an integer from 1 to 3, then dehydrohalogenating the product.

3. A process for preparation of a sulfur-containing O-(meth)acrylate compound according to claim 2, said thioesterification being conducted with a compound having at least two carboxyl groups in its molecule selected from the group consisting of those of the following formulae:

HOOC—$(CH_2)_r$—S—$(CH_2)_s$—S—$(CH_2)_r$—COOH,

HOOC—$(CH_2)_r$—S—S—$(CH_2)_r$—COOH,

HOOC—$(CH_2)_r$—S—$(CH_2)_r$—COOH and

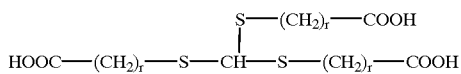

wherein r and s are an integer from 1 to 3.

4. An optical resin composition comprising the sulfur-containing O-(meth)acrylate compound according to claim 1.

5. An optical resin composition according to claim 4, comprising at least one of monomers co-polymerizable with a sulfur-containing O-(meth)acrylate compound and polythiol compounds.

6. An optical resin composition according to claim 5, wherein the co-polymerizable monomer is the compound represented by the following formula (3):

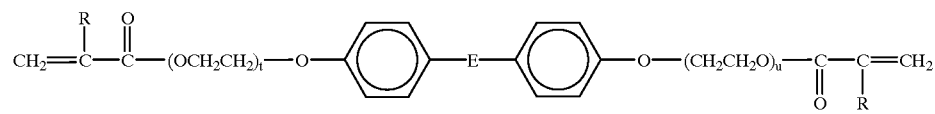

(3)

wherein R represents hydrogen atom or methyl group; t and u represent an integer from 0 to 4; and E represents —$CH_2$—, —$C(CH_3)_2$—, —S— or —$SO_2$—.

7. An optical resin prepared by polymerizing a composition according to claim 6.

8. An optical resin prepared by polymerizing a composition according to claim 5.

9. An optical resin prepared by polymerizing a composition according to claim 4.

10. A lens consisting of an optical resin according to claim 9.

11. A lens consisting of an optical resin according to claim 8.

12. A lens consisting of an optical resin according to claim 7.

* * * * *